United States Patent [19]

Nutter

[11] Patent Number: 5,025,805
[45] Date of Patent: Jun. 25, 1991

[54] NASAL CANNULA ASSEMBLY

[76] Inventor: Betty Nutter, 23218 W. Ditner, Rockwood, Mich. 48173

[21] Appl. No.: 550,894

[22] Filed: Jul. 11, 1990

[51] Int. Cl.$^5$ .............................................. A61M 15/08
[52] U.S. Cl. ......................... 128/207.18; 128/DIG. 26
[58] Field of Search ................... 128/207.18, DIG. 26, 128/200.26, 912

[56] References Cited

U.S. PATENT DOCUMENTS

| | | | |
|---|---|---|---|
| 3,802,431 | 4/1974 | Farr | 128/207.18 |
| 4,535,767 | 8/1985 | Tiep et al. | 128/207.18 |
| 4,699,139 | 10/1987 | Marshall et al. | 128/207.18 |
| 4,739,757 | 4/1988 | Edwards | 128/207.18 |
| 4,827,923 | 5/1989 | Bishop et al. | 128/206.11 |

Primary Examiner—Edgar S. Burr
Assistant Examiner—Stephen R. Funk
Attorney, Agent, or Firm—Dykema Gossett

[57] ABSTRACT

A nasal cannula assembly comprises a nasal cannula with nostril outlet prongs and a pair of oxygen inlets. A pair of oxygen feed tubes at their one ends are connected to the cannula inlets and at their other ends adapted for connection to an oxygen source. Each of the feed tubes have ear contact points intermediate their ends adapted to be looped over the user's ears. A hollow cylindrical cuff of a soft resilient material is mounted over and around each inlet tube and extends between the cannula and the ear contact point to protectively engage the user's nose, face, cheeks and ears to prevent irritation.

5 Claims, 1 Drawing Sheet

U.S. Patent
June 25, 1991
5,025,805
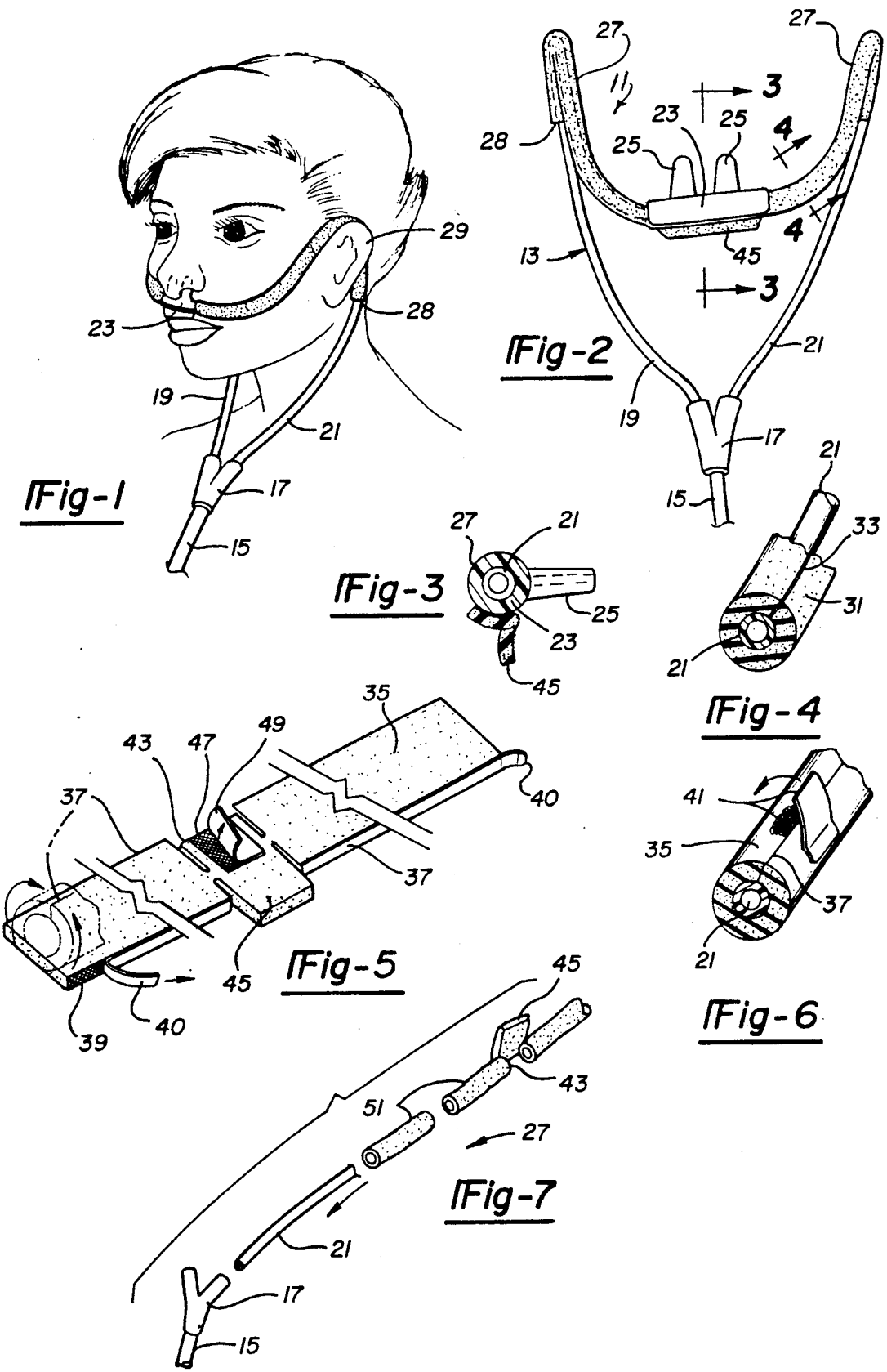

NASAL CANNULA ASSEMBLY

FIELD OF INVENTION

Relates to medical appliances and more particularly to a nasal cannula assembly.

BACKGROUND OF THE INVENTION

When the nasal cannula is used alone with oxygen feed tubes traditionally its use has caused irritation and sores to the patient's nostrils, ears, and face including the cheek bones or cheek areas. This is due to perspiration and pressure of the cannula on the skin of the patients in need of a continuous supply of oxygen.

In previous use of the ordinary cannula there are certain pressure points developed which in addition to perspiration and pressure of the cannula and the outlet tubes upon the user's face, lips, cheeks or ears, lead to skin breakdown and finally sores of the nose, ears and cheek bone areas.

Previously in the use of nasal cannula for the continuous delivery to patients in need of oxygen, the angularity of the cannula prongs with respect to the nostrils is such as to produce unnecessary pressure contact on portions of the nose and nostrils producing discomfort and soreness.

The result is that patients often remove the cannula entirely due to discomfort at periods of time when the continued use of oxygen is believed medically necessary. Efforts have been made to protect the adjacent areas with cotton pads. These frequently fall off or become disassociated from the cannula. Attempts to use a lubricant have been tried. It has been found that the lubricants of the water soluble nature do not contribute to healing of the sores and the small pads are constantly falling out of place. It is these difficulties which interrupt the consistent and continuous oxygen flow and which result in the development of sores in areas where they are difficult to heal.

THE PRIOR ART

Listed below are illustrative prior art patents where there has been some recognition of the problem. Some effort has been made to alleviate this condition:

| Patent No. | Inventor's Name | Date | Description |
| --- | --- | --- | --- |
| 4,535,767 | Tiep, et al. | August 20, 1985 | Oxygen Delivery Apparatus |
| 4,699,139 | Marshall, et al. | October 13, 1987 | Nasal Cannula Assembly with Patent Comfort Pad |
| 4,739,757 | Edwards | April 26, 1988 | Oxygen Tube Retaining Headband |
| 4,827,923 | Bishop, et al. | May 9, 1989 | Protective Facial Mask |

SUMMARY OF THE INVENTION

An important feature of the present invention is to provide a set touch cuff protectively mounted upon the enclosing the oxygen feed tubes for the nasal cannula assembly and extending between the nasal cannula and the portion of the oxygen feed tubes where they supportably extend over the user's ears thereby protectively engaging skin portions of the user's lips, nose, cheeks, face and ears to prevent irritation.

Another feature is to provide a disposable sponge or other absorbent material cover for the plastic oxygen cannula which is mounted over the respective pair of oxygen feed tubes and extends between the nasal cannula and an intermediate portion of the respective tubes to the point where they extend over the user's ears.

A further feature is to provide for the nasal cannula assembly and with respect to the oxygen feed tubes an elongated hollow cylindrical cuff of a soft resilient material which is mounted over and around each of the feed tubes and which extends between the nasal cannula and the intermediate contact point upon the feed tubes where they respectively engage the user's ears thereby protectively engaging the patient's nose, face, cheek and ears and for preventing irritation thereof.

As another feature the present soft touch cuff may be made as one complete unit, as a sleeve initially tubular and slit to fit over and around and enclose the oxygen tubes and extend between the cannula and an intermediate point on the tubes at the point where the tubes engage over the user's ears.

As an alternate, the respective cuff may be formed from an elongated rectangular strip of a disposable or soft resilient material such as sponge material, generally rectangular in shape and having longitudinal side edges. The lateral edge portions of the strip are folded around so as to enclose the exposed portions of the oxygen feed tubes that would normally engage portions of the user's face. The contacting edges of the strip are connected together adhesively or otherwise as to maintain a cylindrical form for the comfort of the user and for preventing skin breakdown or sores from constant use and wear upon the user's nose, face, cheek bones and ears.

It is another feature to provide upon the strip an intermediate cut away portion adapted to supportably receive the nasal cannula to which the respective oxygen feed tubes are connected. The cut away portion provides such sufficient support as will position the nasal prongs at the correct angular position with respect to the nostrils to avoid unnecessary pressure or contact with the interior skin thereof.

A further feature is to provide an improved nasal cannula assembly which will not be rejected by the user so that there is a more consistent oxygen flow as may be required for some patients, and will prevent the developement of sores which are difficult to heal, and which eliminates the conventional discomforts above noted, usages in hospitals, nursing facilities or other use continuously at home.

These and other features and objects will be seen from the following specifications and claims in conjunction with the appended drawings.

THE DRAWINGS

FIG. 1 is a front perspective view of the nasal cannula assembly in a use position.

FIG. 2 is a front elevational view thereof, on an increased scale.

FIG. 3 is a section taken in the direction of arrows 3—3 of FIG. 2 on an increased scale.

FIG. 4 is a fragmentary broken away perspective view taken in the direction of arrows 4—4 of FIG. 2.

FIG. 5 is a perspective view of a strip of resilient material used to make the cuff of FIG. 2.

FIG. 6 is a fragmentary view of a cylindrical tube of resilient material slit to receive and enclose an oxygen feed tube.

FIG. 7 is a fragmentary perspective view of the cuff, feed tube and connector before assembly of the cannula.

DETAILED DESCRIPTION OF OPERATIVE EMBODIMENT

Referring to the drawing, the present nasal cannula device with soft touch protective cuff is generally indicated at 11, FIG 2, and includes a nasal cannula assembly 13.

The oxygen supply conduit 15, of a flexible tubing is connected to a source of pressurized oxygen and joins the connector 17 whose outlets receive the one ends of the oxygen feed tubes 19 and 21, sometimes referred to as the inlet ends of said oxygen feed tubes.

The other ends of the flexible oxygen feed tubes, preferably of a plastic material extend to inlet openings on opposite sides of the conventional nasal cannula 23 which has a pair of nostril outlet prongs 25. One plastic material is polyvinyl chloride.

The foregoing is a conventional construction to which has been applied a cylindrical soft touch cuff 27. One illustrative embodiment cuff 27 surrounds each of the oxygen feed tubes 19 and 21 with their one ends extending to opposite sides of the nasal cannula 23. The other end of each of the cuffs 27 or unit cuff extends to an intermediate point 28 on the respective oxygen feed tubes 19 and 21 which corresponds to where the respective feed tubes extend over lobe portions 29 of the user's ears.

The present cuff 27 is constructed of a soft resilient sponge like or rubber material, preferably of a closed cell construction and which is flexible and of an absorbent material.

As shown in the drawing, the present cuff is in a final form of a cylindrical tube 31 which extends around and encloses the respective oxygen feed tubes 19 and 21. In one embodiment the material from which the cuff is made is in the form of a cylindrical tube 31, FIG. 4, and has along its length a longitudinal slit 33 and such suitable memory and resiliency so that it stays closed. In order to assemble the cylindrical tube 31 around the respective oxygen feed tubes 19 and 21, it is stressed open sufficiently to assemble over the respective oxygen feed tubes and released so that it reassumes the position shown, FIG. 4. This protectively encloses the respective oxygen feed tubes along their length from the points between the cannula 25 and a midpoint 28 on each feed tube where it extends over the user's ear lobe at 29.

Since the cylindrical tube 31 or cuff is of a resilient material, it may be stressed open for assembly over the respective feed tubes 19 and 21 and when released assumes the position shown in the drawing so as to protectively enclose the respective feed tubes. The cuff is adapted for engagement with adjacent areas of the user's mouth, lips, cheeks and ears to avoid irritation thereof.

In the illustrative embodiment showing the cylindrical tube 31 assembled around the respective oxygen feed tubes, the corresponding mating edges adjacent the longitudinal slit 33 are in registry so that the cylindrical tube after assembly retains its cylindrical form, FIG. 4.

Another embodiment of the present surgical cuff is constructed of an elongated rectangular strip 35 of similar material of a flexible nature, such as sponge rubber or the like having opposed longitudinal edges 37. Upon at least one of the longitudinal edges 37, there is applied a layer of a pressure sensitive adhesive 39 or other adhesive which may be covered by the removable protective strip 40, FIG. 5.

At the time of assembly of the strip 35 upon the nasal cannula, the nasal cannula 23 including the adjacent portions of the connected oxygen feed tubes 19 and 21 are centrally positioned over the strip, FIG. 5. The respective longitudinal edges 37 of the strip 35 are rolled into cylindrical form with the respective edges in opposed engaging registry and secured together by adhesive 39.

In place of a pressure sensitive adhesive, it is regarded as equivalent that any other adhesive or cement may be used including VELCRO TM strips 41, FIG. 6, or a suitable adhesive tape. The elongated rectangular strip 35 assumes the cylindrical form shown in the drawing with the nasal cannula 23-25 positioned upon the cut away central portion 43 of the strip and adjacent the positioning flap 45, FIG. 5. A suitable adhesive 47 upon the cut away portions 43, with protective strip 49, anchors cannula 23.

Flap 45 engages the user's upper lip area for properly positioning the nasal cannula 23 so that its prongs 25 extend at a correct angle so as to be spaced within the user's nostrils to minimize wear or irritation of the skin areas.

As a modification of the present cuff, it is contemplated that the cuff could consist of a series of tubular sections 51, FIG. 7, of cylindrical form arranged end to end over and upon the respective oxygen feed tubes and extending from both sides of the nasal cannula 23 to the midpoint portions 28 of the oxygen feed tubes 19 and 21 where they extend around and supportably engage portions of the user's ear lobe 29.

The present soft touch cuff is made of a disposable sponge or other absorbent material in order to protectively cover and enclose the plastic oxygen feed tubes 19 and 21 of the oxygen cannula. This is for the primary purpose of avoiding irritation and sores to the patient's nostrils, mouth, ears, cheekbones or skin areas on the face.

At times the irritation is due to a combination of perspiration of the patient and the pressure of the cannula on the patient's skin.

The present soft touch cuff is adapted to absorb perspiration, providing a dryer field and at the same time cushion all areas of cannula contact with the user's face and nose. This relieves pressure points and avoids skin breakdown and the forming of sores on adjacent areas of the nose, ears and face.

The formation of the flap 45, FIG. 5, on the central cut away portion 43 of the strip 35 is such as to position the nasal cannula 23 to provide a proper angularity of the prongs 25 for the comfort of the patent. One benefit of the present construction is that it provides for a more consistent oxygen flow since the patients are less apt to remove the cannula because of the aching of sores previously produced without the use of some protective cuff along the complete length thereof. Great discomfort heretofore was experienced without such cuff.

The present cuff can be constructed of a resilient sponge-like material which has a thickness in the range of 1/16th to ¼ of an inch, for illustration.

Have described my invention, reference should now be had to the following claims.

I claim:

1. A nasal cannula assembly comprising a nasal cannula having a pair of apertured nostril outlet prongs and a pair of oxygen inlets;

a pair of oxygen feed tubes, each tube having an inlet and an outlet;

the tube outlets being connected to the cannula inlets respectively, and the feed tube inlets being adapted for connection to a source of pressurized oxygen;

each of said feed tubes intermediate their ends adapted to be looped over the user's ears, respectively; and an elongated hollow cylindrical cuff of a soft resilient material mounted over and around each of said feed tubes and extending between said cannula and intermediate its ends, thereby protectively engaging the patient's nose, face, cheek and ears and preventing irritation thereof;

said cuff having therein a partially cutaway portion intermediate its ends to cooperatively receive and support said cannula.

2. In the nasal cannula assembly of claim 1, said cuff including an elongated unit tube having a continuous longitudinal slit along its length, and adapted to be flexed open to receive and enclose said feed tube.

3. In the nasal cannula assembly of claim 1, said cuff including an elongated strip of rectangular shape having upright side edges along its length;

said strip having therein a pair of laterally spaced transverse slits on one side providing a central cutaway portion displaced inwardly of one side edge defining a cannula support;

said strip being rolled into cylindrical form along its length with said upright side edges in snug engagement with each other along their length, thereby surrounding said feed tubes; and a layer of adhesive interconnecting said engaging edges.

4. In the nasal cannula assembly of claim 3, further comprising said strip having a second pair of laterally spaced transverse slots upon its other side providing a lateral support flap for positioning the cannula to elevate its prongs for loose spacing within the user's nostrils.

5. In the nasal cannula assembly of claim 3, further comprising said strip being of a foamed elastomeric material.

* * * * *